United States Patent [19]

Glei et al.

[11] Patent Number: 5,739,817
[45] Date of Patent: *Apr. 14, 1998

[54] METHOD AND APPARATUS FOR DISPLAYING POSITION INFORMATION ADJACENT TO A SCROLL BOX

[75] Inventors: Matthew S. Glei, McMinnville; Colin M. Portnuff, Tualatin; Rommel R. Raj, McMinnville, all of Oreg.

[73] Assignee: Hewlett-Packard Company, Palo Alto, Calif.

[*] Notice: The term of this patent shall not extend beyond the expiration date of Pat. No. 5,581,275.

[21] Appl. No.: 643,660

[22] Filed: May 6, 1996

Related U.S. Application Data

[62] Division of Ser. No. 843,489, Feb. 28, 1992, Pat. No. 5,581,275.

[51] Int. Cl.⁶ ................................................ G06F 3/00
[52] U.S. Cl. ........................................ 345/341; 345/973
[58] Field of Search ................................. 395/326–358; 345/123–125, 121, 973, 326–358

[56] References Cited

U.S. PATENT DOCUMENTS

| | | | |
|---|---|---|---|
| 5,039,937 | 8/1991 | Mandt et al. | 395/341 X |
| 5,095,448 | 3/1992 | Obuchi et al. | 395/341 |
| 5,339,391 | 8/1994 | Wroblewski et al. | 395/341 |
| 5,371,846 | 12/1994 | Bates | 395/341 |
| 5,485,174 | 1/1996 | Henshaw et al. | 345/123 |
| 5,510,808 | 4/1996 | Cina, Jr. et al. | 345/123 |
| 5,532,715 | 7/1996 | Bates et al. | 345/123 |
| 5,550,969 | 8/1996 | Torres et al. | 395/341 |
| 5,581,275 | 12/1996 | Glei et al. | 345/123 |

OTHER PUBLICATIONS

Foley et al., "Computer Graphics: Principles and Practices"; 2nd ed., Addison–Wesley Pub. Co., pp. 374–376, 405–408, 1990.

*Primary Examiner*—John E. Breene
*Attorney, Agent, or Firm*—Curtis G. Rose

[57] ABSTRACT

A method and apparatus for locating a predetermined position in a computer file. A continuous, static ECG waveform is displayed in rows on a CRT screen. A scroll bar permits a user to use a computer mouse to click and drag the scroll box to display different portions of the ECG data. When the cursor is on the scroll box and a button on the mouse is depressed, a data window opens adjacent the scroll box and displays the hours, minutes and seconds of the time of day when the ECG waveform of the portion currently displayed was recorded. The data window moves with the scroll box and continues to display current time of the data displayed. When the mouse button is released, the data window closes and the screen changes to display ECG waveform from the newly selected time.

6 Claims, 5 Drawing Sheets

METHOD AND APPARATUS FOR DISPLAYING POSITION INFORMATION ADJACENT TO A SCROLL BOX

CROSS REFERENCE TO RELATED APPLICATION

This is a divisional of application Ser. No. 07/843,489 filed on Feb. 28, 1992, now U.S. Pat. No. 5,581,275.

BACKGROUND OF THE INVENTION

1. Field of the Invention

The present invention relates to methods and apparatus for locating a predetermined position in a computer file and more particularly to such methods and apparatus in which a scroll box is moved to locate and display a position in the file.

2. Description of the Related Art

In a Holter ECG monitoring system, a patient is fitted with a monitor which detects and stores continuous ECG waveforms. Sometimes several leads are connected to the patient so that two or more such waveforms are recorded. It is not unusual for such a monitor to be worn for many hours thereby generating thousands of periodic heartbeat waveforms which are stored for later review to assist in diagnosis and treatment of the patient.

Scroll boxes are commonly used for locating and displaying a portion of a file in windowing programs such as Microsoft Windows™ and MOTIF™. A scroll bar indicates the possible area to be viewed and a scroll box positioned on the scroll bar indicates the position of that portion of the file in the window relative to total file length. In a word processing program if the scroll box is halfway down the scroll bar it indicates that the screen is displaying a portion from approximately the middle of the document. An operator uses a mouse to position a cursor on the scroll box, depresses a button on the mouse, and moves the mouse thereby moving the scroll box so long as the mouse button is depressed. Such mouse movement moves the box relative to the scroll bar. When the mouse button is released, a new portion of the file corresponding to the new scroll box position is displayed in the window.

The difficulty with this totally qualitative approach is that the user often bumbles around, successively approximating position in the file and then paging up or down to find an exact position. This often requires the user to take a stab at the position using the scroll box, look for a frame of reference (document contents, time, etc.) and then correct the selection. Another alternative to this is a Go to function often found in applications. The user selects Go to and a new scroll box appears. The user has an exact position readout (in, e.g., pages or time) available as the scroll box moves along a scroll bar. However, the user must be fairly dexterous to move the box accurately while observing the time displayed, especially when the box is not directly under the time readout.

SUMMARY OF THE INVENTION

A method for locating a predetermined position in a computer file in which a portion of the file is displayed in a window having a scroll box on one side for varying that portion of the file displayed in the window. The scroll box is engaged with a cursor and a relatively small data window is opened adjacent the scroll box when it is so engaged. The data window includes data which indicates the position of that portion of the file displayed in the window. Scroll box movement changes the data in the data window.

The present invention is advantageous in that it provides both a qualitative and quantitative approach to locating a predetermined position in a computer file. In addition, the data window, which provides the quantitative information, opens adjacent a scroll box and remains adjacent thereto as the scroll box is moved to display a different portion of the file in the window.

The foregoing and other objects, features and advantages of the invention will become more readily apparent from the following detailed description of a preferred embodiment which proceeds with reference to the drawings.

DETAILED DESCRIPTION OF THE PREFERRED EMBODIMENT

Figure 1:
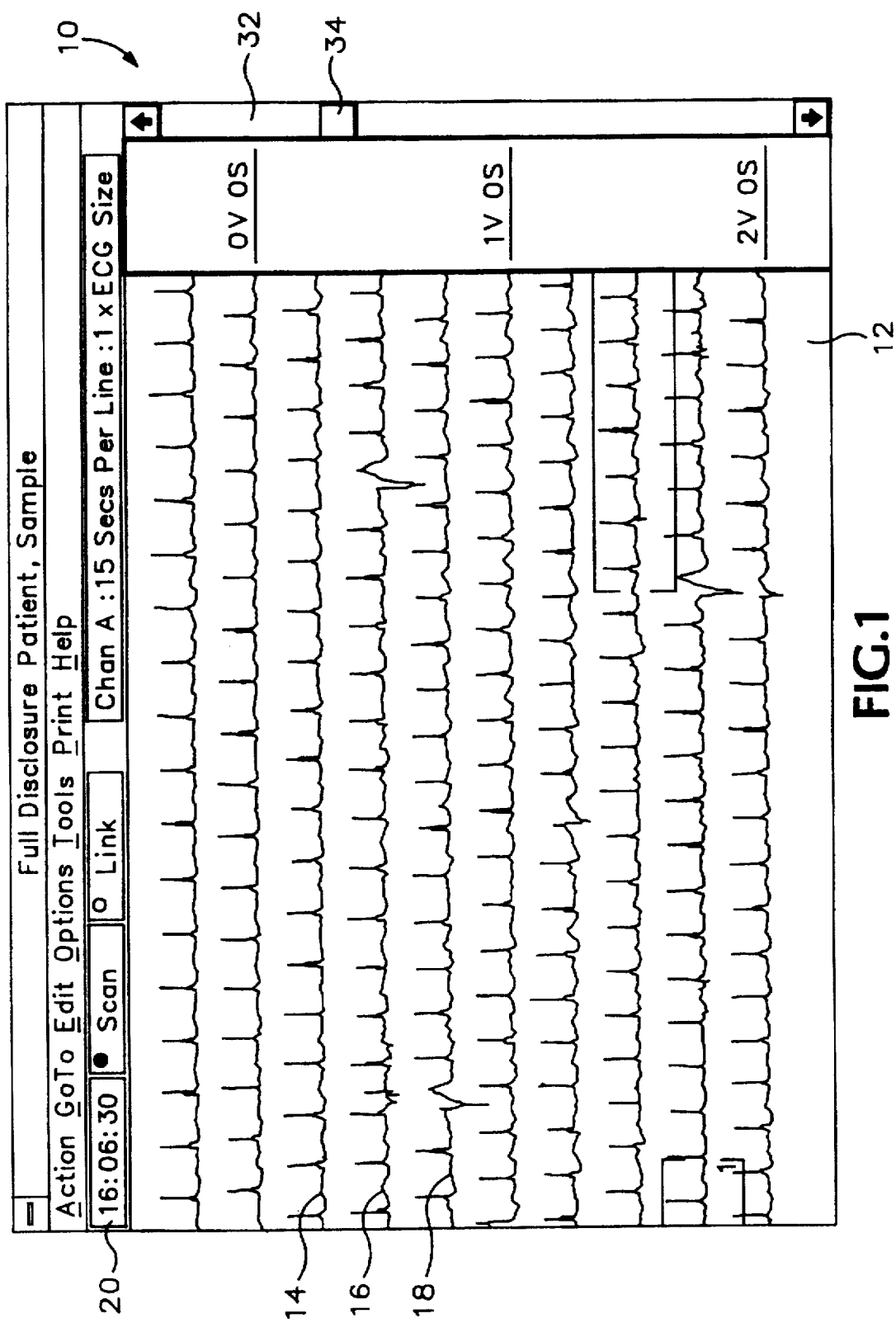
FIG. 1 is a display on a cathode ray tube (CRT) pursuant to the present invention.

Turning now to FIG. 1, indicated generally at 10, is a display formed on a CRT screen incorporated into a system constructed in accordance with the present invention. The present embodiment of the invention comprises a personal computer having an Intel™386 processor, a keyboard, a color VGA monitor, a mouse, and a Microsoft Windows™ graphical user interface. The computer is programmed, in a manner which is described in more detail hereinafter, to operate in accordance with the following description of the preferred embodiment.

Prior to describing the manner in which the computer program, represented by the chart of FIG. 5, controls the system, description will first be made of the user interface and of the manner in which the present embodiment is used to display heartbeat waveforms contained in stored ECG data.

The stored ECG data to be analyzed is collected by a Holter monitor which is fitted to a patient for detecting and storing a continuous ECG waveform for many hours. The Holter monitor includes a peak detector which locates the R-wave of each heartbeat waveform. The continuous ECG waveform, comprised of a plurality of individual heartbeat waveforms, is stored in chronological order. After a predetermined amount of data is collected in the Holter monitor, it is removed from the patient and connected to the system of the present invention in a known manner for transferring the ECG waveform, as well as the information, including the R-wave locations, generated by a preliminary analysis performed by the monitor, to the system computer.

Display screen 10 includes a window 12 in which a continuous ECG waveform is displayed. The waveform data is generated on a Holter monitor as described above and is transferred to the system in which screen 10 is incorporated. The continuous ECG waveform is displayed in a plurality of static rows, like rows 14, 16, 18. The waveform is displayed in chronological order, i.e., the order of occurrence of each of the R-waves, which are the pulses that can be observed on each row, is from left to right within each row. The next R-wave in chronological order after the right-most end of row 14 is the first R-wave appearing on row 16. Similarly, the right end of row 16 continues on row 18 and so forth. It is to be appreciated that the ECG waveform displayed in window 12 comprises only approximately 2-3 minutes worth of collected ECG data. The displayed data thus comprises only a small portion of the entire record of the continuous ECG waveform which can be collected for a period of 24 hours or more. The entire stored record of the continuous ECG waveform in chronological order is referred to herein as a computer file.

A problem which a clinician examining a computer file faces is how to display predetermined portions of the file in window 12, which as noted may comprise only 2-3 minutes out of 24 hours worth of data. For example, the present embodiment of the invention includes a time button 20 which displays the time of occurrence day of the first R-wave on the top row of window 12. In FIG. 1 this R-wave occurred at 16 hours, 6 minutes and 30 seconds (16:06:30 military time or 4:06:30 in the afternoon) on the day of monitoring. The present embodiment of the invention provides two ways to display different portions of the computer file containing the ECG data.

Figure 2:
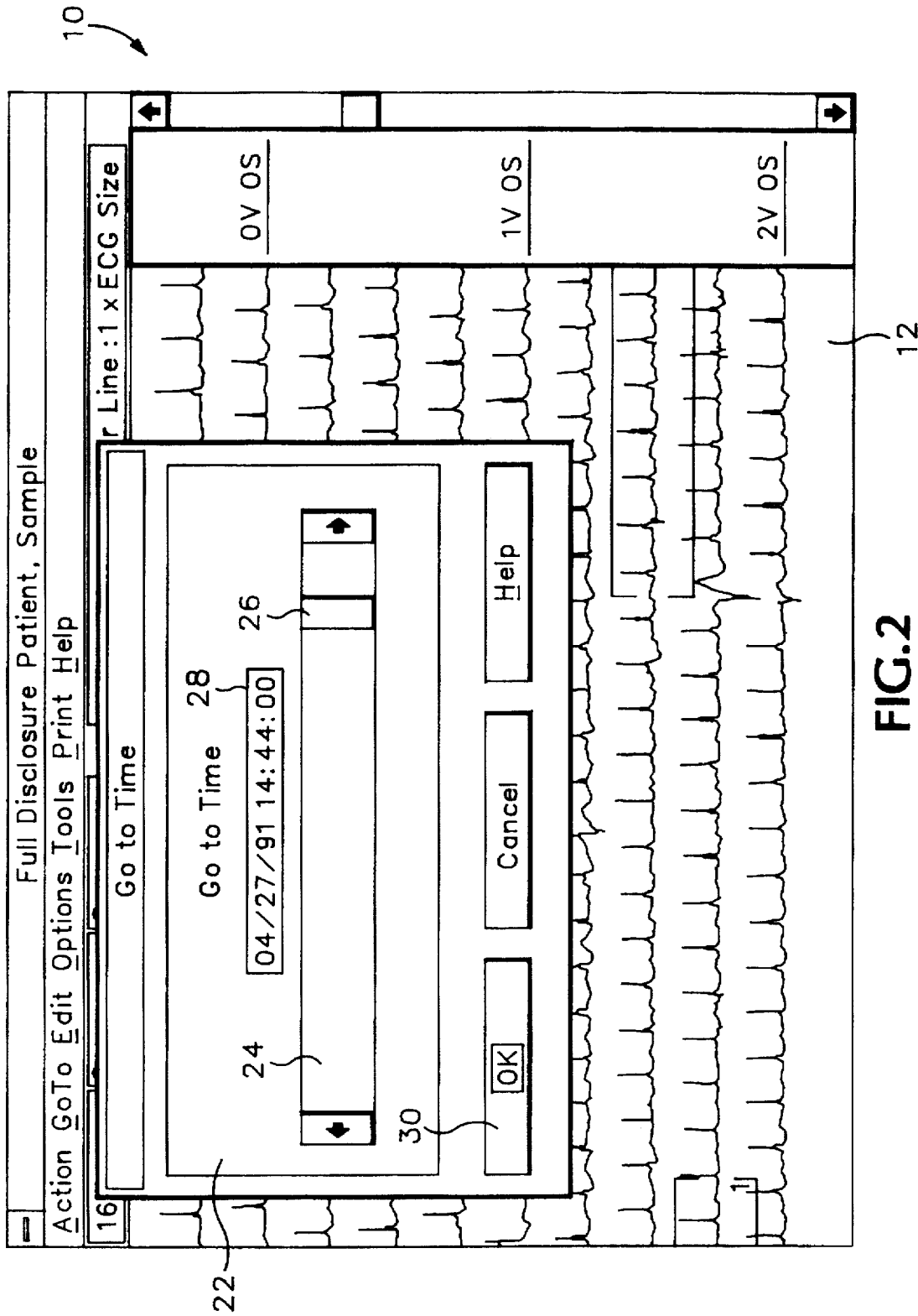
FIG. 2 is a display similar to FIG. 1 having an open Go to panel thereon.

First, a cursor (not shown in FIG. 1) is positioned on button 20 using the mouse which comprises part of the system in which screen 10 is incorporated. When the cursor is so positioned, the mouse is clicked and a GO to Time pane; 22, in FIG. 2, appears as shown in FIG. 2. Included thereon is a scroll bar 24, a scroll box 26 and a time-display readout As is known in the art, scroll bar 24 is proportional to the lengths of the file displayed in window 12 with the position of scroll box 26 on the scroll bar determining what portion of the file is displayed in window 12. For example, with scroll box 26 at the fight-most end of the scroll bar, the very end of the file is displayed in window 12; with scroll box 26 at the left-most end of the scroll bar, the very beginning of the file is displayed in window 12; and with the scroll box substantially mid-way between the fight and left ends of the scroll bar, a portion from the middle of the file is displayed in window 12.

As is also known in the art, scroll box 26 is moved by positioning the cursor thereon, depressing a mouse button and moving the mouse with the button depressed, a mouse operation referred to herein as clicking and dragging the scroll box. Thus, the scroll bar 24 and scroll box 26 provide a user with a qualitative technique for displaying approximate portions of the file in window 12.

As scroll box 26 moves, the time displayed in readout 28 changes to indicate the exact time of the first-occurring R-wave in window 12 which will be displayed. Thus readout 28 provides a quantitative technique for accurately locating an exact position. When scroll box 26 is located as desired and/or the time in readout 28 is set as desired, the cursor is positioned on an OK button 30 and the mouse clicked thereby changing that portion of the file in window 12 pursuant to the setting on panel 22 and closing the panel. Using this approach may be somewhat disadvantageous in that it is difficult to simultaneously observe the relative position of scroll box 26 on scroll bar 24 and the time in readout 28.

Returning again to FIG. 1, consideration will now be made of a second feature for displaying a predetermined position in a computer file in accordance with the present invention. Screen 10 includes thereon a scroll bar 32 having a scroll box 34 positioned thereon. As with scroll bar 24 and scroll box 26, when scroll box 34 is positioned at the top of scroll bar 32, the very first portion of the ECG waveform appears in window 12. With box 34 at the very bottom of bar 32 the very end of the ECG waveform appears in the window and with box 34 mid-way between the top and the bottom a middle portion of the collected ECG data is displayed. Box 34 is also moved by positioning the cursor on the box and dragging it with the mouse to a new vertical position along bar 32.

Figure 3:
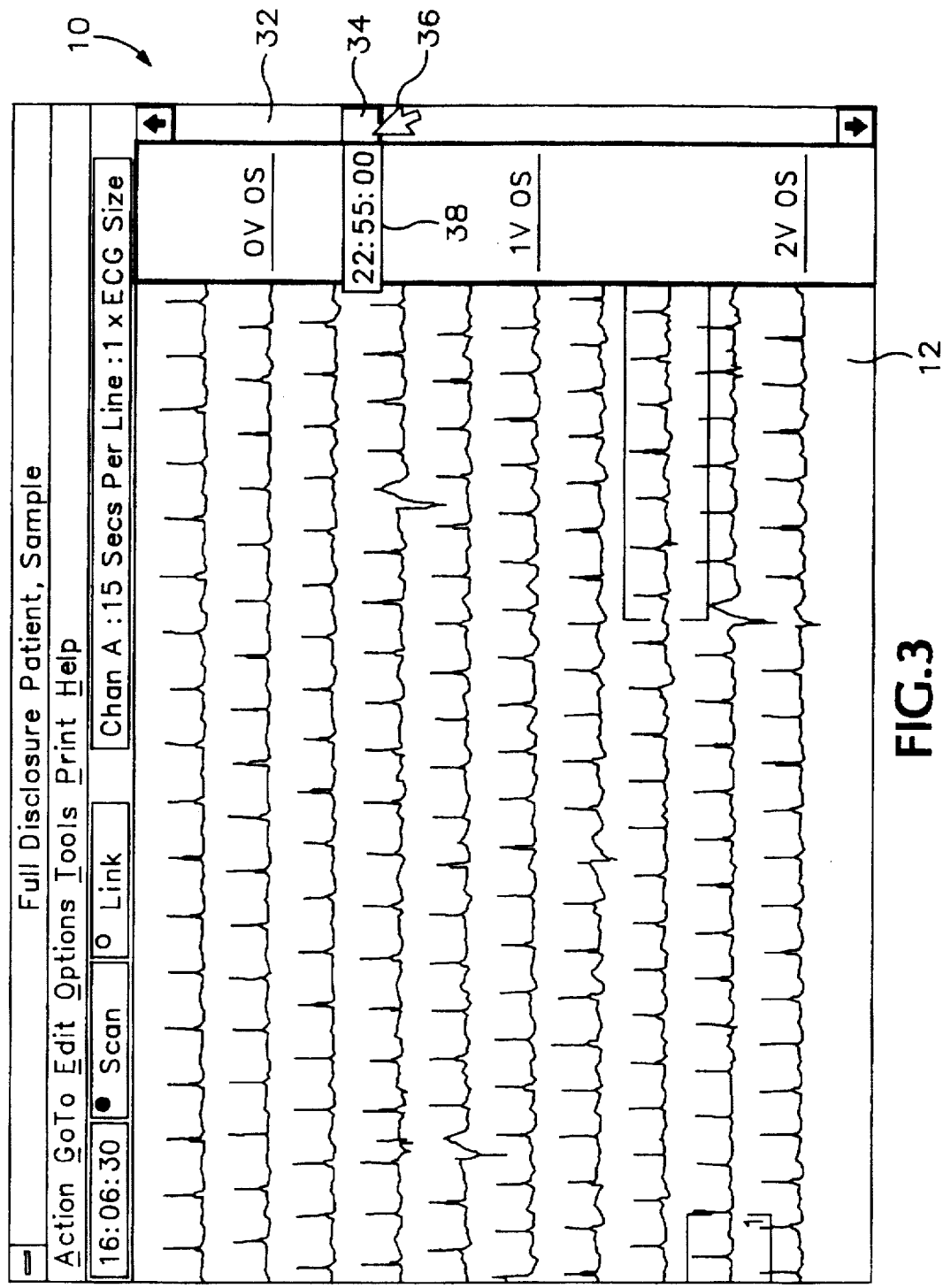
FIG. 3 is a view similar to FIG. 1 illustrating a scroll box engaged with a cursor.

Turning now to FIG. 3, a cursor 36 is shown engaged with scroll box 34. The cursor is engaged with the scroll box by positioning it thereover and depressing a button on the mouse. For so long as the button remains depressed, movement of the mouse so as to cause vertical movement of cursor 36 moves box 34 vertically along scroll bar 32.

Also for so long as cursor 36 is engaged with box 34, a data window 38 is open adjacent the scroll box as shown. Units of time, in hours, minutes and seconds are displayed in data window 38. The time in the data window is the time of day of the occurrence of the first R-wave on the top row of the ECG waveform in window 12. As box 34 moves responsive to movement of cursor 36, data window 38 retains the same position relative to box 34 as shown in FIG. 3, i.e., data window 38 moves with the scroll box. Further, the time in data window 38 changes to indicate the current time of the first R-wave in window 12 as scrolling proceeds.

Figure 4:
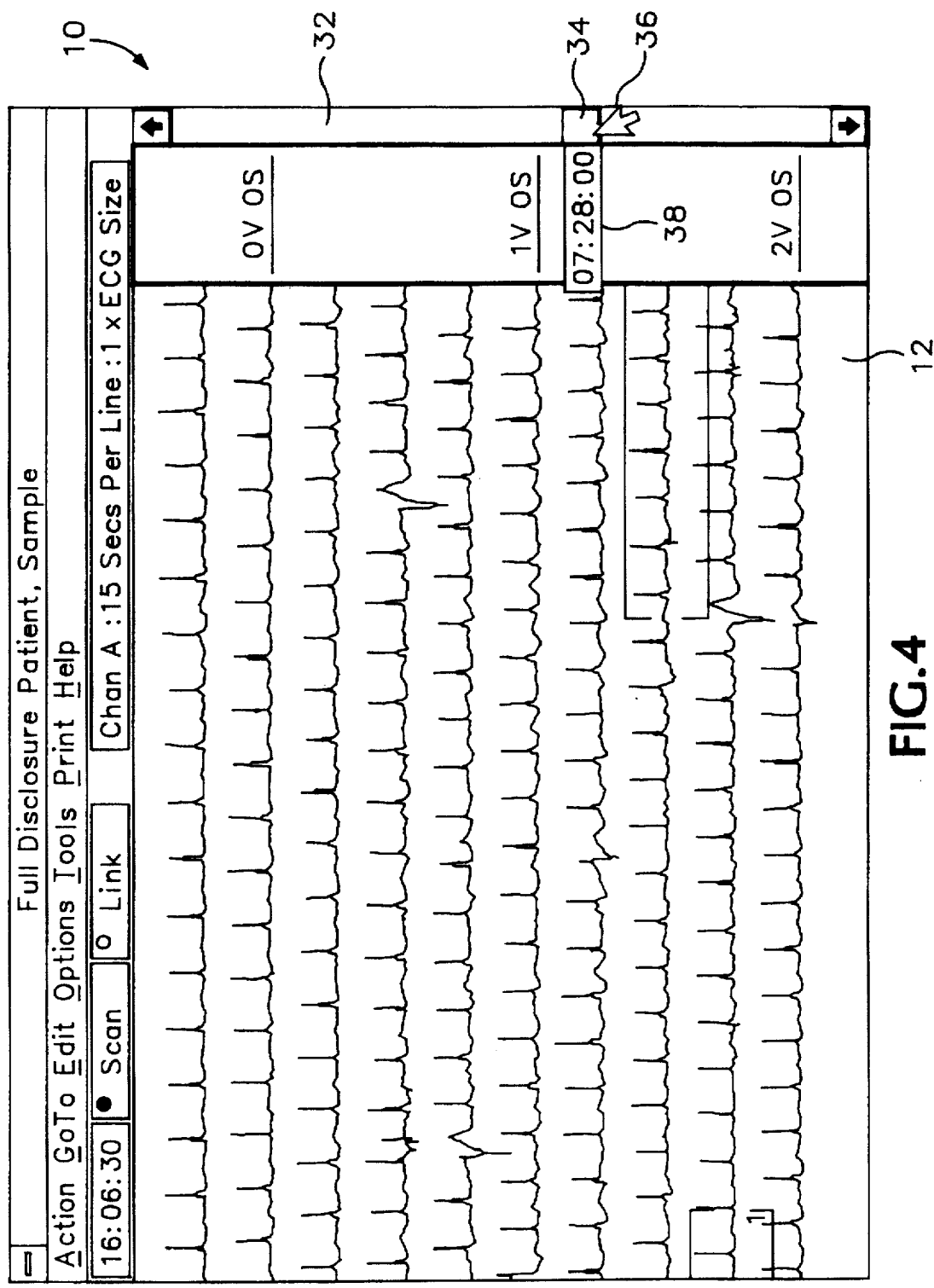
FIG. 4 is a view similar to FIG. 3 after the scroll box is dragged for displaying a different portion of a file

Turning now to FIG. 4, box 34 is indicated in a new position relative to scroll bar 32 with cursor 36 still engaging the box. Window 38 remains open and indicates the new time of data that will be displayed in window 12 when the mouse button is released. When cursor 36 is disengaged from box 34, i.e., when the mouse button is released, data window 38 closes and the data from the selected time is displayed. Such operation permits a user to approximate the desired file position by relative positioning of box 34 on scroll bar 32 and to observe time in data window 38 while so doing which facilitates easier, and therefore faster, location of a predetermined position in a file relative to prior art methods.

Figure 5:
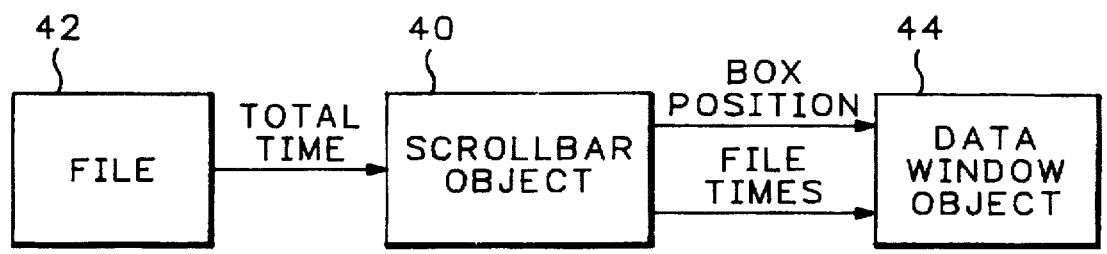
FIG. 5 is a schematic chart depicting operation of a computer program which in part implements the present embodiment of the invention.

Looking now at FIG. 5, illustrated therein is a chart which depicts operation of a program used to control the computer in the present embodiment of the invention. The program depicted in FIG. 5 was written in C, a language which is used to implement the object-oriented design of the present embodiment of the invention. The program was written for use with Windows 3.0™, supplied by Microsoft Corporation, using the developer's tool provided for use in writing programs for use with the Windows 3.0™ graphical user interface. The terms used in the following description are those used by persons having ordinary skill in the design and implementation of computer programs in object-oriented languages. It should, however, be appreciated that the present invention may be implemented by a computer programmed with object-oriented languages or otherwise or may be implemented entirely with hardware.

If FIG. 5, indicated generally at 40 is a commercially available scroll-bar object 40. The scroll-bar object comprises a set of computer code which defines scroll bar 32 and scroll box 34 on CRT screen 10. A file 42 represents the code and data which displays the continuous ECG waveform in window 12. As will be recalled, this file includes the time of occurrence of each R-wave in hours, minutes and seconds on the monitoring date. The difference between the occurrence of the first and last R-waves in the file, i.e., the total time in the file, is provided to the scroll-bar object.

The scroll-bar object provides two types of information to a data-window object 44. The data-window object comprises code and accompanying data which opens data window 38 responsive to cursor engagement of scroll box 34. Information provided to data-window object 34 by scroll-bar object 40 includes scroll box position and file time. The scroll box position is provided in device coordinates, i.e., pixels, and provides information to the data-window object concerning the relative position of scroll box 34 on scroll bar 32. Scroll-bar object 40 uses the total time from file 42 to compute a time position based on scroll box position with the total time being proportional to the length of scroll bar 32 and the file time, i.e., that portion of the file displayed in window 12, being proportional to the position of scroll box 34 on scroll bar 32.

Data-window object 44 includes code which defines data window 38 as follows. The data window is always right-justified against scroll box 34 as shown in FIG. 4. Data-window object 44 uses the box position information from scroll-bar object 40 to maintain data window 38 in substantially the same vertical position as scroll box 34 as can be seen in comparing the different vertical positions of scroll box 34 in FIGS. 3 and 4. Data-window object 44 also converts the file time information from scroll-bar object 40, which is provided to object 44 in seconds, to an hours: minutes: seconds format and displays the same as shown in FIGS. 3 and 4. Finally, information concerning the font-size of the numbers used to display hours, minutes and seconds in dam window 38 is provided to dam-window object 44. Such information is used by the data object to define the vertical and horizontal size of the window to minimize the size of data window 38 while making certain that the numerals appearing therein are all visible.

Having illustrated and described the principles of my invention in a preferred embodiment thereof, it should be readily apparent to those skilled in the art that the invention can be modified in arrangement and detail without departing from such principles.

I claim all modifications coming within the spirit and scope of the accompanying claims:

1. A program storage medium readable by a computer, said program storage medium tangibly embodying a program of instructions executable by said computer to perform method steps for locating a predetermined position in a computer file, said method steps comprising:

displaying a portion of the file in a window having a scroll box on one side thereof for varying which portion of the file is displayed in the window;

engaging and moving the scroll box with a cursor;

automatically opening a relatively small data window adjacent the scroll box in response to engagement and movement of the scroll box with the cursor;

displaying data in the data window indicative of a position of that portion of the file displayed within the window;

moving the scroll box thereby changing the data in the data window until said predetermined position is located; and automatically closing said relatively small data window in response to disengagement of said scroll box with said cursor.

2. The program storage medium of claim 1, further comprising the method step of moving the data window responsive to scroll box movement thereby maintaining substantially the same relative position between the scroll box and the data window.

3. An article of manufacture, comprising:

a program storage medium having a computer readable program code embodied therein for locating a predetermined position in a computer file, said computer readable program code further comprising:

a scroll bar object for defining a scroll bar and a scroll box;

a data window object for opening a data window responsive to cursor engagement of said scroll box;

said scroll bar object providing a scroll box position to said data window object;

said scroll bar object determining file positional information based on said scroll box position and providing said file positional information to said data window object; and said data window object placing said file positional information in said data window.

4. The article of manufacture of claim 3, wherein said data window object moves the data window responsive to scroll box movement thereby maintaining substantially the same relative position between the scroll box and the data window.

5. An article of manufacture, comprising:

a program storage medium having a computer readable program code embodied therein for locating a predetermined position in a computer file, said computer readable program code interacting with a computer operating system, said computer operating system having a scroll bar object for defining a scroll bar and a scroll box, said computer readable program code further comprising:

a data window object for opening a data window responsive to cursor engagement of said scroll box;

said data window object receiving a scroll box position from said scroll box object;

said data window object receiving file positional information based on said scroll box position from said scroll box object; and said data window object placing said file positional information in said data window.

6. The article of manufacture of claim 5, wherein said data window object moves the data window responsive to scroll box movement thereby maintaining substantially the same relative position between the scroll box and the data window.

* * * * *